(12) United States Patent
Huelskamp et al.

(10) Patent No.: US 10,245,135 B2
(45) Date of Patent: Apr. 2, 2019

(54) SEGMENTED SKIRTED SURGICAL MESH

(71) Applicants: BG Medical, LLC, Barrington, IL (US); Aspide Medical S.A.S., La Talaudière (FR)

(72) Inventors: John W. Huelskamp, Barrington, IL (US); Eric Nelson, Barrington, IL (US); Eric Bouillet, La Talaudière (FR); William Wiecek, La Talaudière (FR)

( * ) Notice: Subject to any disclaimer, the term of this patent is extended or adjusted under 35 U.S.C. 154(b) by 396 days.

(21) Appl. No.: 14/325,969

(22) Filed: Jul. 8, 2014

(65) Prior Publication Data

US 2015/0012019 A1 Jan. 8, 2015

Related U.S. Application Data

(60) Provisional application No. 61/843,771, filed on Jul. 8, 2013, provisional application No. 61/845,191, filed on Jul. 11, 2013.

(51) Int. Cl.
*A61B 17/08* (2006.01)
*A61F 2/00* (2006.01)

(52) U.S. Cl.
CPC .................. *A61F 2/0063* (2013.01)

(58) Field of Classification Search
CPC .. A61F 2/0063; A61F 2/00; A61F 2002/0071; A61F 2002/0081; A61F 2002/0086; A61F 2002/009; A61B 17/0057
See application file for complete search history.

(56) References Cited

U.S. PATENT DOCUMENTS

| 751,415 A | 2/1904 | Prindle |
| 2,330,693 A | 9/1943 | Erdely |
| 4,333,471 A | 6/1982 | Nakai |
| 5,264,218 A | 11/1993 | Rogozinski |

(Continued)

FOREIGN PATENT DOCUMENTS

| CA | 2201439 | 7/2004 |
| EP | 0783270 | 6/2004 |

(Continued)

*Primary Examiner* — Gregory Anderson
(74) *Attorney, Agent, or Firm* — Pandiscio & Pandiscio

(57) ABSTRACT

A segmented skirted surgical mesh for use in reconstructing a soft tissue defect, the segmented skirted surgical mesh comprising:
a base layer of surgical mesh, the base layer of surgical mesh comprising an outer edge; and
a segmented continuous skirt of surgical mesh comprising an outer edge and an inner edge which defines a central opening, the segmented continuous skirt of surgical mesh being secured to the base layer of surgical mesh at the outer edge of the continuous skirt of surgical mesh, and the segmented continuous skirt of surgical mesh comprising a plurality of slits formed in the segmented continuous skirt of surgical mesh, wherein the plurality of slits extend outwardly from the inner edge of the segmented continuous skirt of surgical mesh, whereby to form a plurality of flaps of surgical mesh in the segmented continuous skirt of surgical mesh, such that at least one of the flaps of surgical mesh can be lifted away from the base layer of surgical mesh and secured to soft tissue without causing distortion of the base layer of surgical mesh.

7 Claims, 14 Drawing Sheets

(56) References Cited

U.S. PATENT DOCUMENTS

| | | |
|---|---|---|
| 5,634,931 A | 6/1997 | Kugel |
| 5,769,864 A | 6/1998 | Kugel |
| D399,965 S | 10/1998 | Laughlin et al. |
| D403,774 S | 1/1999 | Laughlin et al. |
| 5,916,225 A | 6/1999 | Kugel |
| D416,327 S | 11/1999 | Kugel |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,224,616 B1 | 5/2001 | Kugel |
| D445,188 S | 7/2001 | Walter |
| 6,280,453 B1 | 8/2001 | Kugel et al. |
| 6,290,708 B1 | 9/2001 | Kugel et al. |
| 6,420,622 B1 | 7/2002 | Johnston et al. |
| 6,790,213 B2 | 9/2004 | Cherok et al. |
| 6,884,212 B2 | 4/2005 | Thierfelder et al. |
| 7,396,975 B2 | 7/2008 | Sigurjonsson et al. |
| 8,182,545 B2 | 5/2012 | Cherok et al. |
| 2002/0052649 A1 | 5/2002 | Greenhalgh |
| 2003/0130745 A1 | 7/2003 | Cherok et al. |
| 2003/0212460 A1* | 11/2003 | Darois ............... A61F 2/0063 623/23.64 |
| 2008/0147099 A1* | 6/2008 | Uen ..................... A61F 2/0063 606/151 |
| 2011/0288567 A1 | 11/2011 | Ranucci et al. |
| 2012/0232334 A1 | 9/2012 | Bell et al. |
| 2013/0218125 A1* | 8/2013 | Stopek ............... A61F 2/0063 604/500 |
| 2013/0267970 A1 | 10/2013 | Cardinale et al. |

FOREIGN PATENT DOCUMENTS

| | | |
|---|---|---|
| EP | 2730297 | 5/2014 |
| WO | WO 0232346 | 4/2002 |
| WO | WO 2010/039249 | 4/2010 |

* cited by examiner

SEGMENTED SKIRTED SURGICAL MESH

REFERENCE TO PENDING PRIOR PATENT APPLICATIONS

This patent application:

(i) claims benefit of prior U.S. Provisional Patent Application Ser. No. 61/843,771, filed Jul. 8, 2013 by BG Medical, LLC and John W. Huelskamp et al. for SEGMENTED SKIRTED HERNIA MESH; and (ii) claims benefit of prior U.S. Provisional Patent Application Ser. No. 61/845,191, filed Jul. 11, 2013 by BG Medical, LLC and John W. Huelskamp et al. for SEGMENTED SKIRTED HERNIA MESH.

The two (2) above-identified patent applications are hereby incorporated herein by reference.

FIELD OF THE INVENTION

This invention relates to medical procedures and apparatus in general, and more particularly to medical procedures and apparatus for repairing soft tissue defects such as abdominal hernias and the like.

BACKGROUND OF THE INVENTION

In the reconstruction of soft tissue defects in humans and animals, such as in abdominal hernia repairs, surgical mesh is often used to reinforce the soft tissue defect so as to facilitate healing and to prevent subsequent defect recurrence. More particularly, when performing a closure of a soft tissue defect in an anatomical wall (e.g., to repair an abdominal hernia), it is common to secure a surgical mesh to the soft tissue at the edge of the soft tissue defect, with some overlap between the surgical mesh and the soft tissue, so as to increase the healed strength of the surgical repair. The surgical mesh is typically secured to the soft tissue adjacent to the soft tissue defect with suture or tacks.

In practice, and looking now at FIGS. 1-3, in open procedures the soft tissue reconstruction is typically carried out using a "skirted" surgical mesh 5. Skirted surgical mesh 5 generally comprises a base layer 10 of surgical mesh terminating in an outer edge 12, and a continuous "skirt" or rim 15 of surgical mesh terminating in an outer edge 17 and an inner edge 18 which defines a central opening 19. Continuous skirt or rim 15 overlies the outer portion of base layer 10 (e.g., so that outer edge 17 of continuous skirt or rim 15 is substantially aligned with outer edge 12 of base layer 10), and continuous skirt or rim 15 is secured to base layer 10 only at or adjacent to outer edge 17 of continuous skirt or rim 15, such that the inner portions of continuous skirt or rim 15 (i.e., the portions adjacent to inner edge 18) can be lifted away from base layer 10 when desired. As a result, continuous skirt or rim 15 provides an easily accessed section of surgical mesh which facilitates fixation of skirted surgical mesh 5 to the soft tissue, i.e., by fixing continuous skirt or rim 15 of skirted surgical mesh 5 to the edges of the soft tissue defect using conventional suture or tack fixation. By providing skirted surgical mesh 5 with the continuous skirt or rim 15 of mesh material, when skirted surgical mesh 5 is being secured to the soft tissue, the sharp ends of the fixation elements (e.g., the suture needle or tack) are isolated from the delicate internal organs of the patient by base layer 10, whereby to prevent inadvertent damage to the delicate internal organs of the patient.

However, it has been found that when pulling up on continuous skirt or rim 15 of skirted surgical mesh 5 (e.g., for suturing and/or tacking), this pulling up of the continuous skirt or rim 15 can cause base layer 10 to distort significantly (e.g., to transform from a smooth planar configuration to a curved configuration, such as is shown in FIG. 4). Such distortion in base layer 10 of skirted surgical mesh 5 can make it difficult to provide a flat, symmetrical repair which is smooth and comfortable for the patient. More particularly, the configurations of surgical mesh used in these types of soft tissue repairs (e.g., the hernia meshes used in abdominal hernia repairs) are normally circular or oval in shape (FIGS. 2-4 show exemplary surgical meshes which are oval in shape) and can possess very tight radii, particularly at the longitudinal ends 25 of oval skirted surgical meshes 5 (see FIGS. 2 and 4). As the radii of continuous skirt or rim 15 of skirted surgical mesh 5 becomes tighter, the effect of "pulling up" on the continuous skirt or rim 15 of skirted surgical mesh 5 (e.g., with graspers 30, FIG. 4) is increasingly distorting to base layer 10 of skirted surgical mesh 5.

Efforts have been made to reduce this distortion of base layer 10 of skirted surgical mesh 5 when pulling up on continuous skirt or rim 15 of skirted surgical mesh 5.

In one such effort, and looking now at FIG. 5, the inner edge 18 of continuous skirt or rim 15 is scalloped (i.e., a portion of inner edge 18 of continuous skirt or rim 15 is recessed, such as is shown in FIG. 5 at 40, from the remainder of inner edge 18 in an effort to minimize the distortion of base layer 10 of skirted surgical mesh 5 when pulling up on continuous skirt or rim 15 of skirted surgical mesh 5. Unfortunately, in practice, this approach has proven to be of limited benefit.

In another such effort, and looking now at FIG. 6, a surgical mesh 45 is provided which comprises a base layer 50 of surgical mesh which is completely covered with a top layer 55 of surgical mesh, with top layer 55 being secured to base layer 50 about the outer edge(s) 60 of the two layers, and with top layer 55 being bifurcated at 65 so as to provide two separate pockets of surgical mesh. Then, during use, a first half of top layer 55 of surgical mesh 45 is pulled upward for fixation (e.g., by gripping the first half of top layer 55 with graspers 30 at the bifurcation line 65) and then the second half of the top layer 55 of surgical mesh 45 is pulled upward for fixation (e.g., by gripping that second half of top layer 55 with graspers 30 at bifurcation line 65). Unfortunately, this construction still suffers from distortion of base layer 50 when one or both halves of top layer 55 of surgical mesh 45 is drawn upward for fixation.

Thus there is a need for a novel surgical mesh which provides a skirt or rim of surgical mesh about the outer perimeter of a base layer of surgical mesh but which allows the skirt or rim of surgical mesh to be pulled upward without distorting the smooth planar configuration of the base layer of surgical mesh.

SUMMARY OF THE INVENTION

The present invention comprises the provision and use of a novel surgical mesh which provides a skirt or rim of surgical mesh about the outer perimeter of a base layer of surgical mesh but which allows the skirt or rim of surgical mesh to be pulled upward without distorting the smooth planar configuration of the base layer of surgical mesh.

In one preferred form of the invention, there is provided a segmented skirted surgical mesh for use in reconstructing a soft tissue defect, the segmented skirted surgical mesh comprising:

a base layer of surgical mesh, said base layer of surgical mesh comprising an outer edge; and a segmented continuous skirt of surgical mesh comprising an outer edge and an inner edge which defines a central opening, said segmented continuous skirt of surgical mesh being secured to said base layer of surgical mesh at said outer edge of said segmented continuous skirt of surgical mesh, and said segmented continuous skirt of surgical mesh comprising a plurality of slits formed in said segmented continuous skirt of surgical mesh, wherein said plurality of slits extend outwardly from said inner edge of said segmented continuous skirt of surgical mesh, whereby to form a plurality of flaps of surgical mesh in said segmented continuous skirt of surgical mesh, such that at least one of said flaps of surgical mesh can be lifted away from said base layer of surgical mesh and secured to soft tissue without causing distortion of said base layer of surgical mesh.

In another preferred form of the invention, there is provided a method for reconstructing a soft tissue defect, the method comprising:

providing a segmented skirted surgical mesh comprising:
a base layer of surgical mesh, said base layer of surgical mesh comprising an outer edge; and
a segmented continuous skirt of surgical mesh comprising an outer edge and an inner edge which defines a central opening, said segmented continuous skirt of surgical mesh being secured to said base layer of surgical mesh at said outer edge of said segmented continuous skirt of surgical mesh, and said segmented continuous skirt of surgical mesh comprising a plurality of slits formed in said segmented continuous skirt of surgical mesh, wherein said plurality of slits extend outwardly from said inner edge of said segmented continuous skirt of surgical mesh, whereby to form a plurality of flaps of surgical mesh in said segmented continuous skirt of surgical mesh, such that at least one of said flaps of surgical mesh can be lifted away from said base layer of surgical mesh and secured to soft tissue without causing distortion of said base layer of surgical mesh;
positioning said segmented skirted surgical mesh adjacent to a soft tissue defect; and
lifting at least one of said flaps of surgical mesh away from said base layer of surgical mesh and securing said at least one flap of surgical mesh to soft tissue without causing distortion of said base layer of surgical mesh.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 1:
FIG. 1 is a schematic view showing a soft tissue defect being reconstructed using a surgical mesh.
Figure 2:
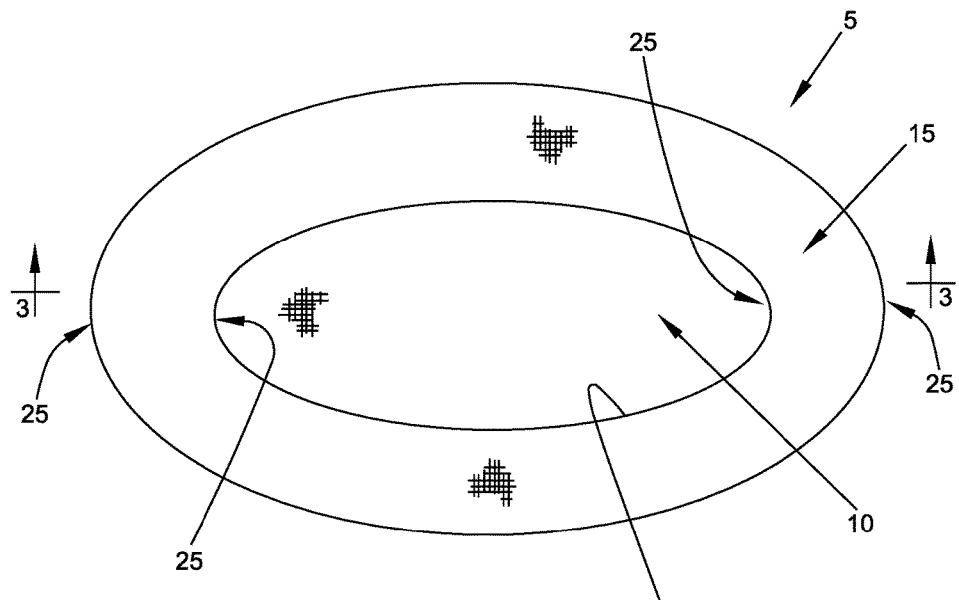
FIGS. 2 and 3 are schematic views showing a prior art skirted surgical mesh in greater detail.
Figure 3:
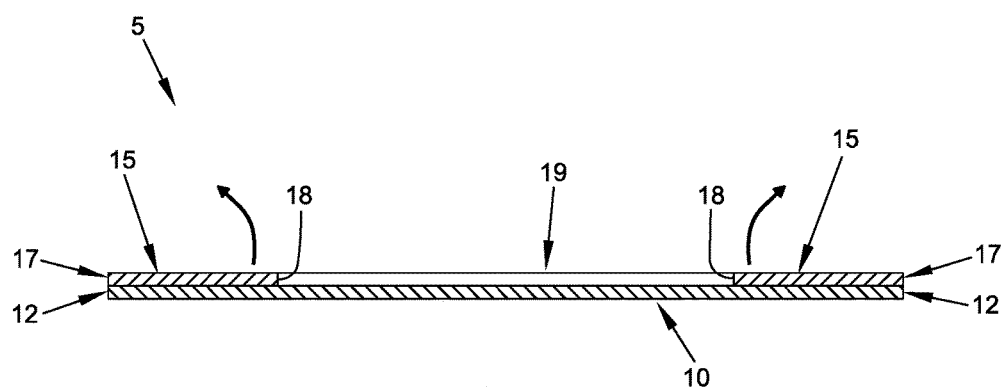
Figure 4:
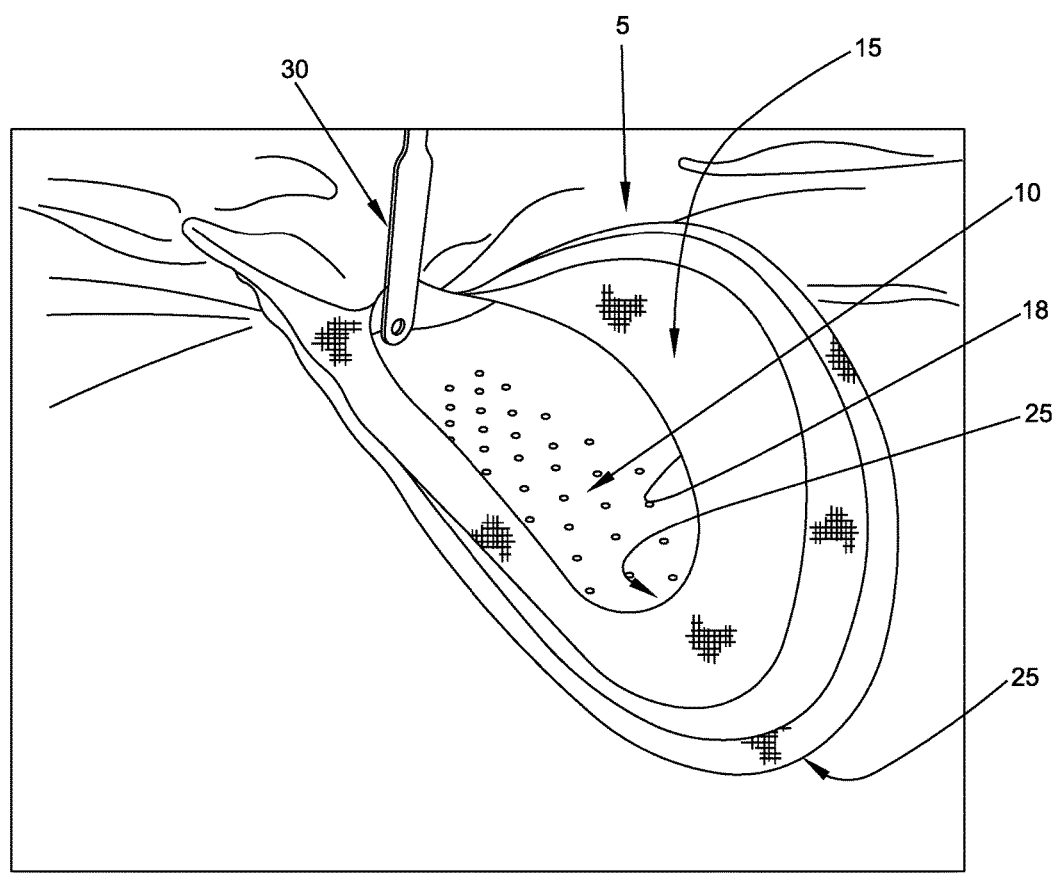
FIG. 4 is a schematic view showing the prior art skirted surgical mesh of FIGS. 2 and 3 becoming distorted as the continuous skirt or rim of the skirted surgical mesh is lifted away from the base layer of the skirted surgical mesh.
Figure 5:
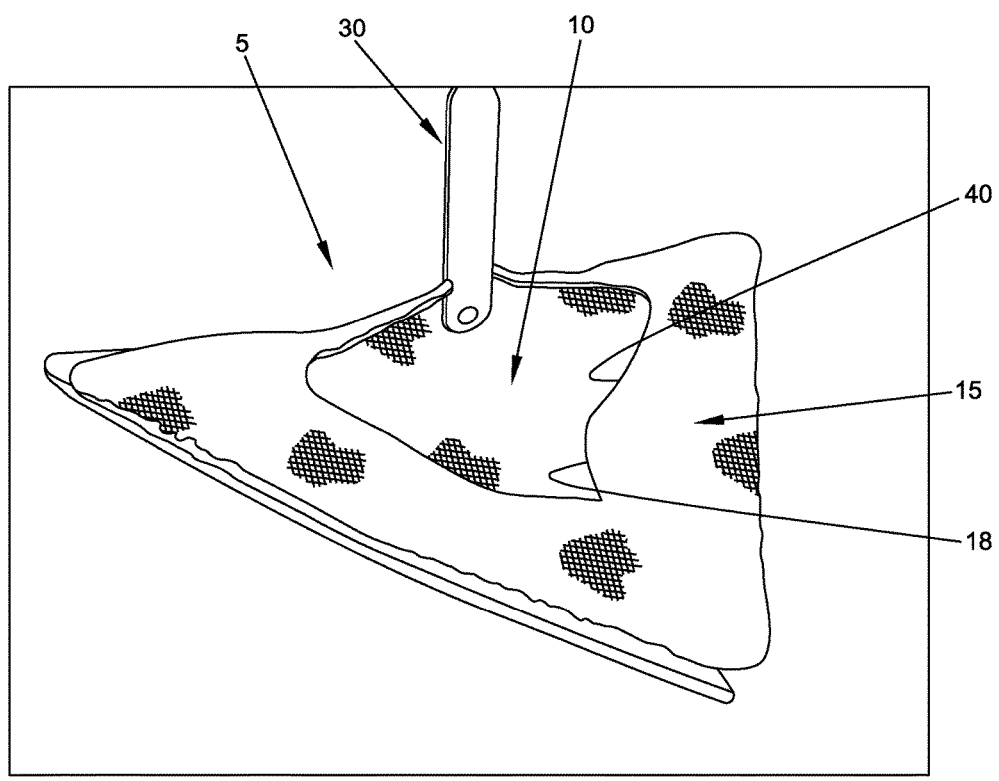
FIG. 5 is a schematic view showing a prior art skirted surgical mesh wherein the inner edge of the continuous skirt or rim of the surgical mesh is scalloped in an effort to minimize distortion of the base layer of the skirted surgical mesh as the continuous skirt or rim of the skirted surgical mesh is lifted away from the base layer of the skirted surgical mesh.
Figure 6:
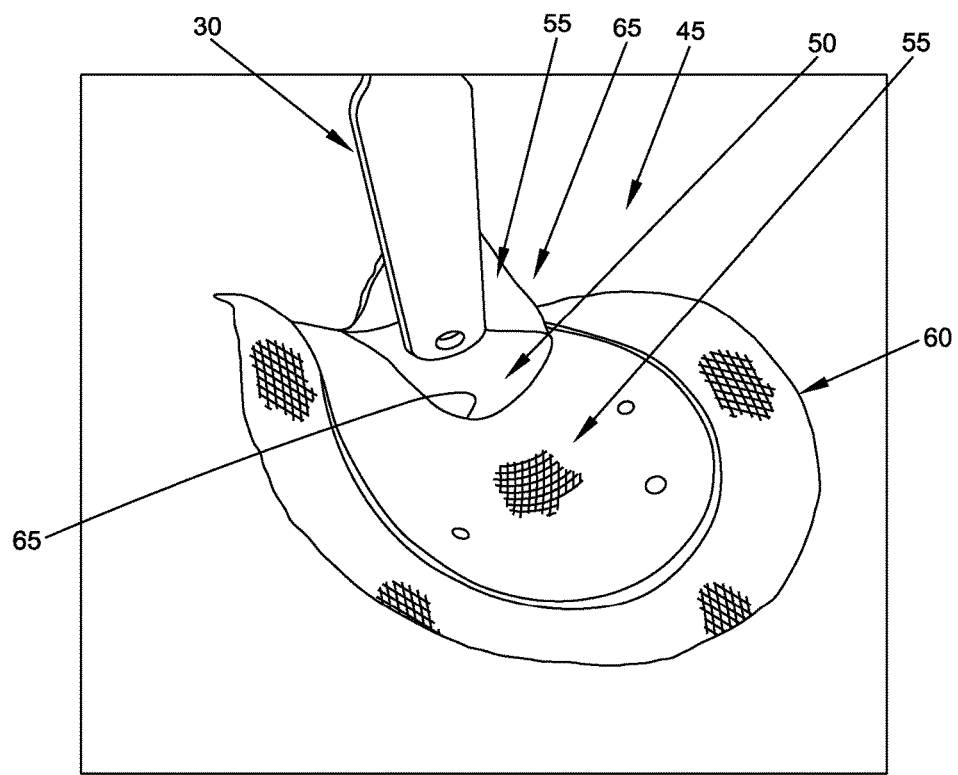
FIG. 6 is a schematic view showing a prior art surgical mesh which comprises a base layer of surgical mesh which is completely covered with a top layer of surgical mesh, with the top layer of surgical mesh being secured to the base layer of surgical mesh about the outer edges of the two layers, and with the top layer of surgical mesh being bifurcated so as to provide two separate pockets of surgical mesh.
Figure 7:
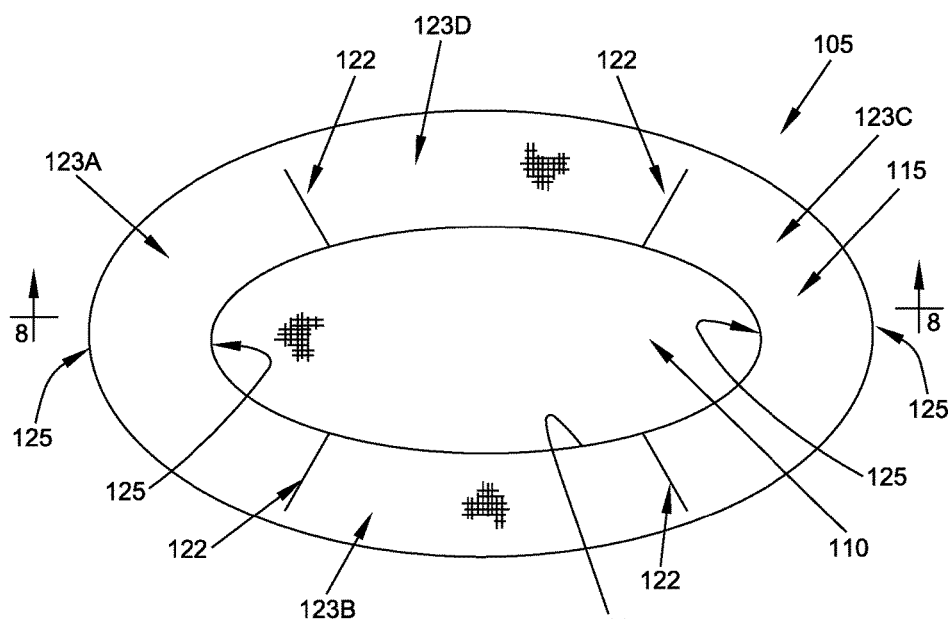
FIGS. 7-10 are schematic views showing a novel segmented skirted surgical mesh formed in accordance with the present invention.
Figure 8:
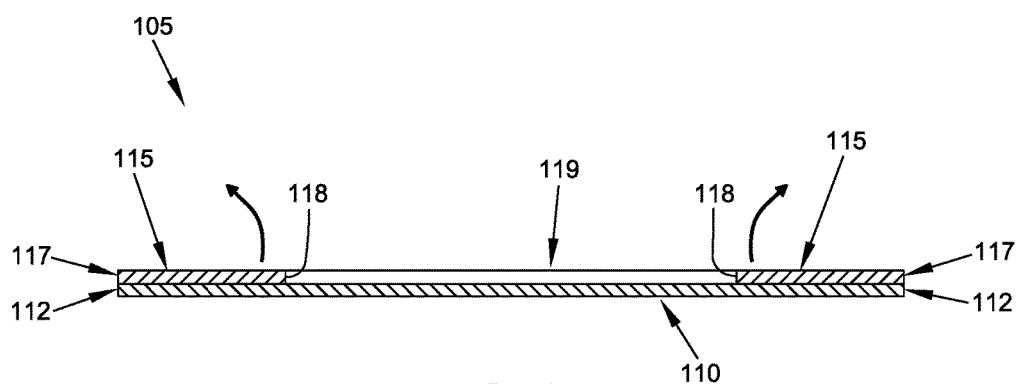
Figure 9:
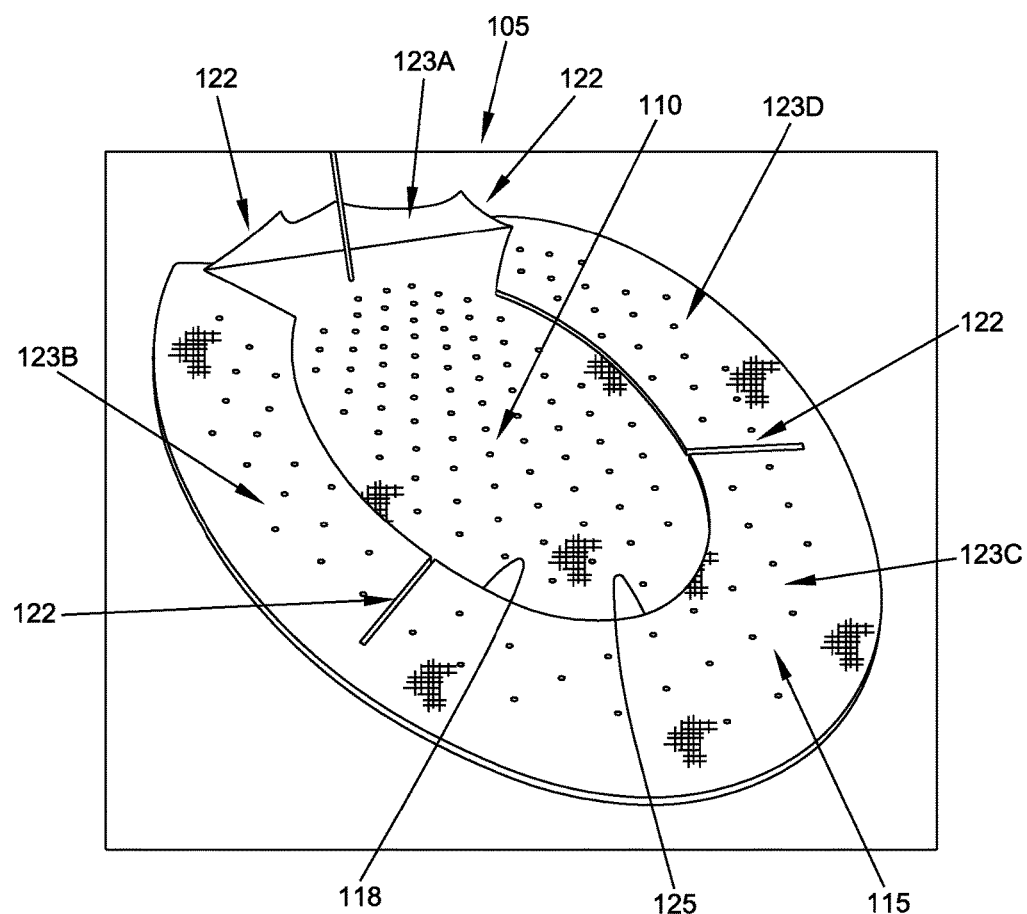
Figure 10:
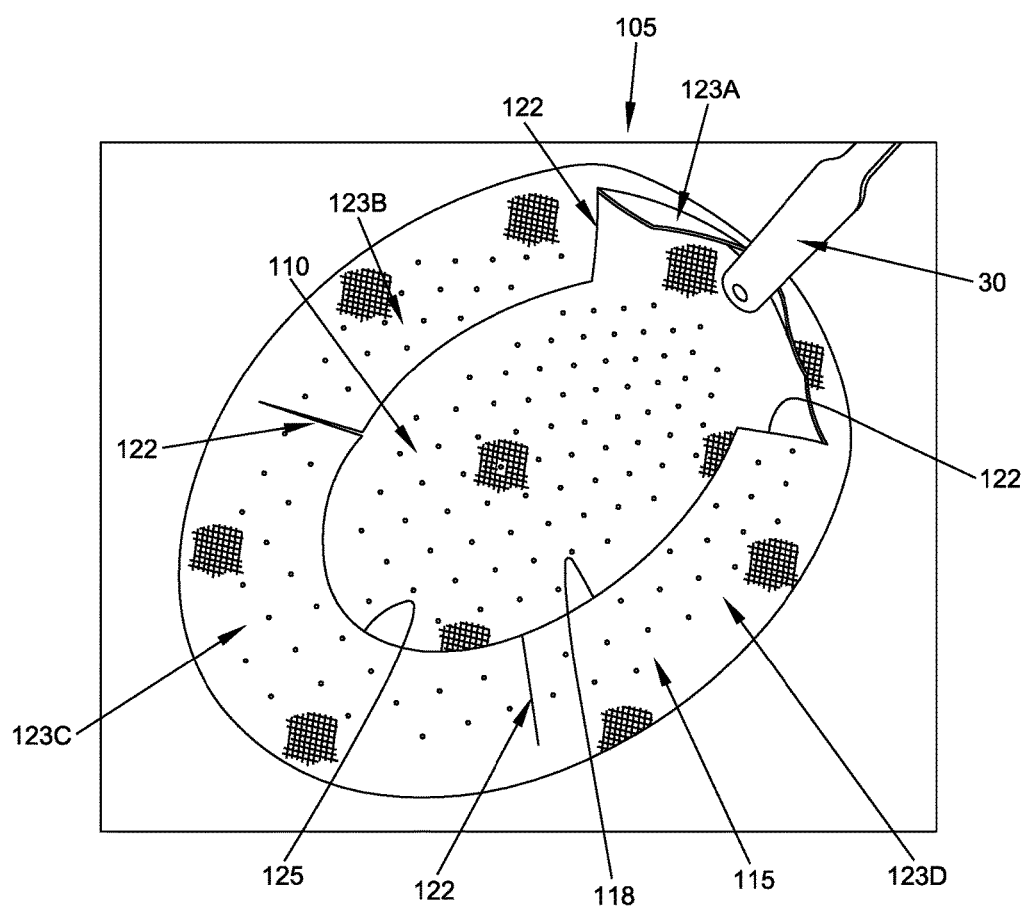

The present invention comprises the provision and use of a novel surgical mesh which provides a skirt or rim of surgical mesh about the outer perimeter of a base layer of surgical mesh but which allows the skirt or rim of surgical mesh to be pulled upward without distorting the smooth planar configuration of the base layer of surgical mesh.

More particularly, and looking now at FIGS. 7-10, the present invention comprises the provision and use of a novel segmented skirted surgical mesh 105. Novel segmented skirted surgical mesh 105 comprises a base layer 110 of surgical mesh terminating in an outer edge 112, and a segmented continuous skirt or rim 115 of surgical mesh terminating in an outer edge 117 and an inner edge 118 which defines a central opening 119. Segmented continuous skirt or rim 115 overlies the outer portion of base layer 110 (e.g., so that outer edge 117 of segmented continuous skirt or rim 115 is substantially aligned with outer edge 112 of base layer 110), and segmented continuous skirt or rim 115 is secured to base layer 110 only at or adjacent to outer edge 117 of segmented continuous skirt or rim 115, such that the inner portions of segmented continuous skirt or rim 115 (i.e., the portions adjacent to inner edge 118) can be lifted away from base layer 110 when desired.

The segmented continuous skirt or rim 115 of surgical mesh is segmented by providing a plurality of breaks or cuts or slits 122 in the continuity of segmented continuous skirt or rim 115 of surgical mesh 105, whereby to form a plurality of segments or flaps 123A, 123B, 123C, etc. of the segmented continuous skirt or rim 115. In one preferred form of the invention, there are at least three breaks or cuts or slits 122 in the continuity of segmented continuous skirt or rim 115 of surgical mesh 105, whereby to form at least three segments or flaps 123A, 123B, 123C, etc.

Each of the segments or flaps 123A, 123B, 123C, etc. of segmented continuous skirt or rim 115 provides an easily accessed section of surgical mesh which facilitates fixation of segmented skirted surgical mesh 105 to the soft tissue, i.e., by fixing the various segments or flaps 123A, 123B, 123C, etc. of segmented continuous skirt or rim 115 to the edges of the soft tissue defect using conventional suture or tack fixation. By providing segmented skirted surgical mesh 5 with the segmented continuous skirt or rim 115 of surgical mesh, when segmented skirted surgical mesh 105 is being secured to the soft tissue, the sharp ends of the fixation elements (e.g., the suture needle or tack) are isolated from the delicate internal organs of the patient by base layer 110 of segmented skirted surgical mesh 105, whereby to prevent inadvertent damage to the delicate internal organs of the patient. At the same time, and significantly, by providing a segmented continuous skirt or rim 115 of surgical mesh, where the segmented continuous skirt or rim 115 is segmented (through the provision of breaks or cuts or slits 122) into a plurality of segments or flaps 123A, 123B, 123C, etc., distortion of base layer 110 of segmented skirted surgical mesh 105 can be reduced or eliminated when segmented continuous skirt or rim 115 is pulled upward, since then only the surgical mesh of a particular segment or flap 123A, 123B, 123C, etc. is pulled upward—the remainder of the segments or flaps 123A, 123B, 123C, etc. of the segmented continuous skirt or rim 115 are unaffected, which results in reduced distortion of base layer 110 of segmented skirted surgical mesh 105.

By way of example but not limitation, having three or four evenly-spaced breaks or cuts or slits 122 in segmented continuous skirt or rim 115 of a small oval or circular segmented skirted surgical mesh 105 keeps base layer 110 of segmented skirted surgical mesh 105 substantially flat even when some or all of segments or flaps 123A, 123B, 123C, etc. of the segmented continuous skirt or rim 115 is lifted up from base layer 110 of segmented skirted surgical mesh 105 (FIGS. 7-10), since then only the surgical mesh of a particular segment or flap 123A, 123B, 123C, etc. is pulled upward—the remainder of the segments or flaps 123A, 123B, 123C, etc. are unaffected, which results in reduced distortion of base layer 110 of segmented skirted surgical mesh 105.

In larger constructions, an oval configuration (FIGS. 7-10) is typically used, inasmuch as defects in a body wall cavity (e.g., an abdominal hernia) are typically oblong in shape (due to the stress orientation in the soft tissue). These oval configurations have opposing tight end radii 125 which benefit even more than circular configurations by providing breaks or cuts or slits 122 in segmented continuous skirt or rim 115.

Figure 11:
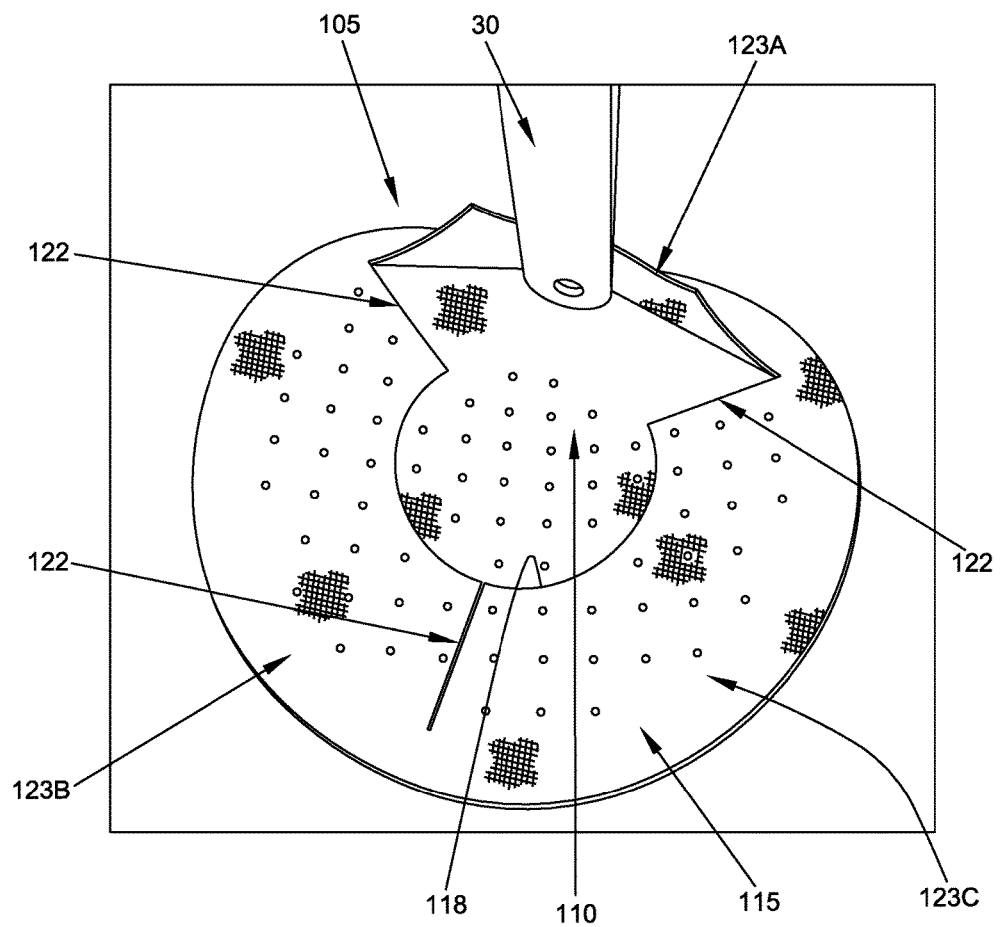
FIGS. 11 and 12 are schematic views showing another novel segmented skirted surgical mesh formed in accordance with the present invention.
Figure 12:
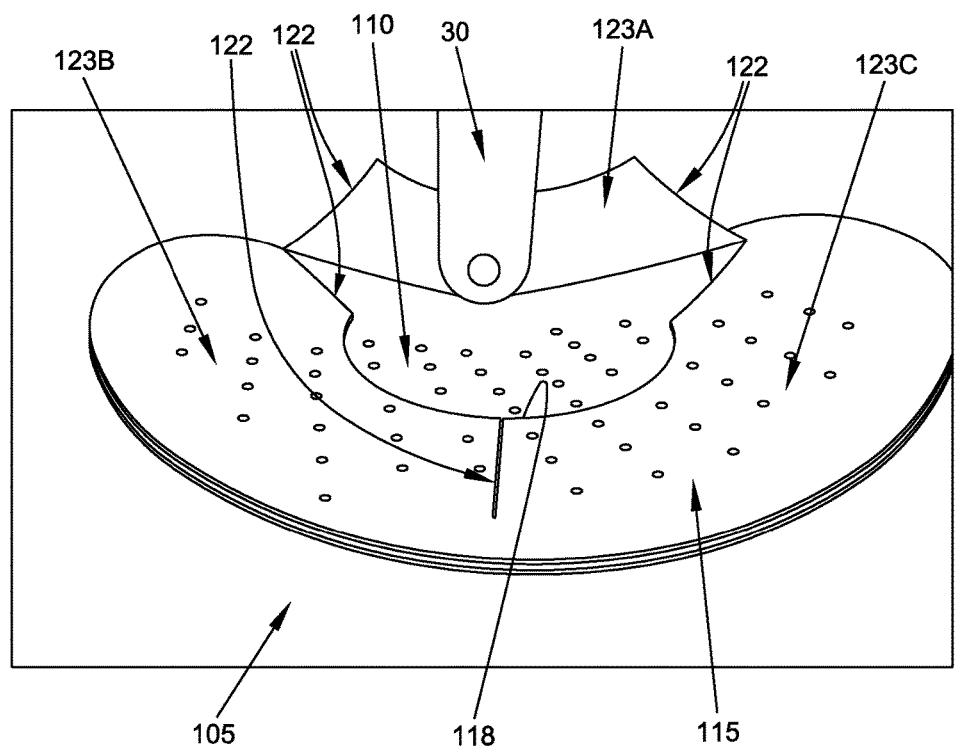

FIGS. 11 and 12 show a segmented skirted surgical mesh 105 having a circular configuration. Note that the segmented continuous skirt or rim 115 of segmented skirted surgical mesh 105 of FIGS. 11 and 12 has three breaks or cuts or slits 122, whereby to provide three segments or flaps 123A, 123B and 123C.

The breaks or cuts or slits 122 in segmented continuous skirt or rim 115 of segmented skirted surgical mesh 105 are preferably accomplished by cutting through segmented continuous skirt or rim 115, preferably starting at inner edge 118 of segmented continuous skirt or rim 115 and extending radially outwardly, and preferably terminating just short of the outer edge 117 of segmented continuous skirt or rim 115. In one preferred embodiment, breaks or cuts or slits 122 extend at an angle of 90 degrees to the adjacent inner edge 118 of segmented continuous skirt or rim 115. Alternatively, the breaks or cuts or slits 122 in segmented continuous skirt or rim 115 may be made at varying angles to inner edge 118 of segmented continuous skirt or rim 115 so as to further minimize distortion in base layer 110 of segmented skirted surgical mesh 105 when segments or flaps 123A, 123B, 123C, etc. are subjected to lifting away from base layer 110.

Figure 13:
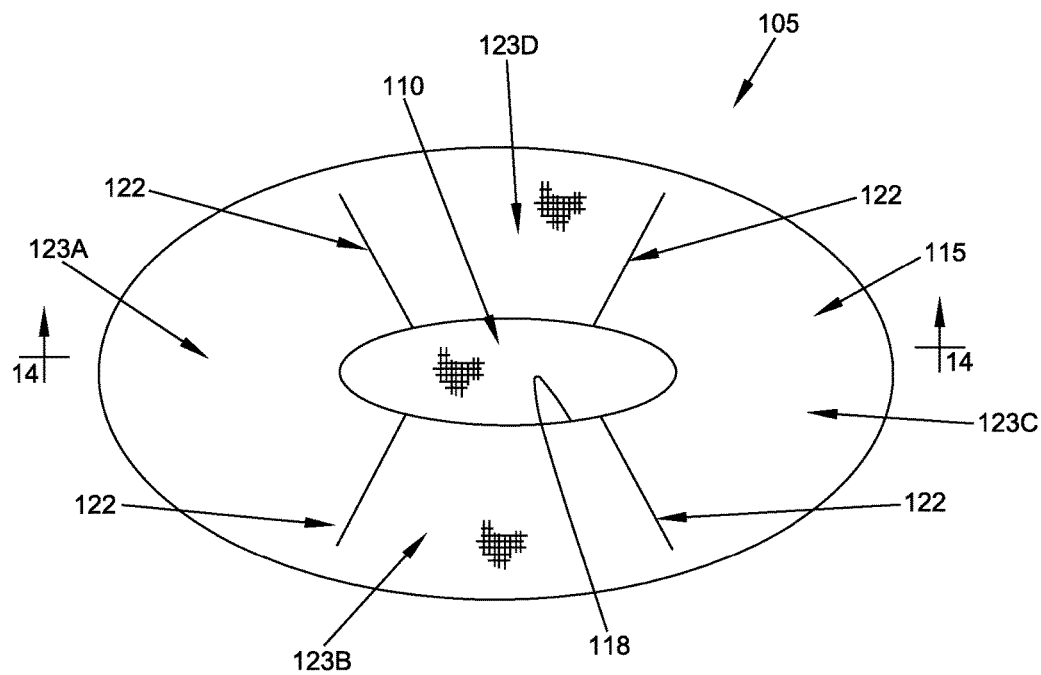
FIGS. 13-15 are schematic views showing another novel segmented skirted surgical mesh formed in accordance with the present invention.
Figure 14:
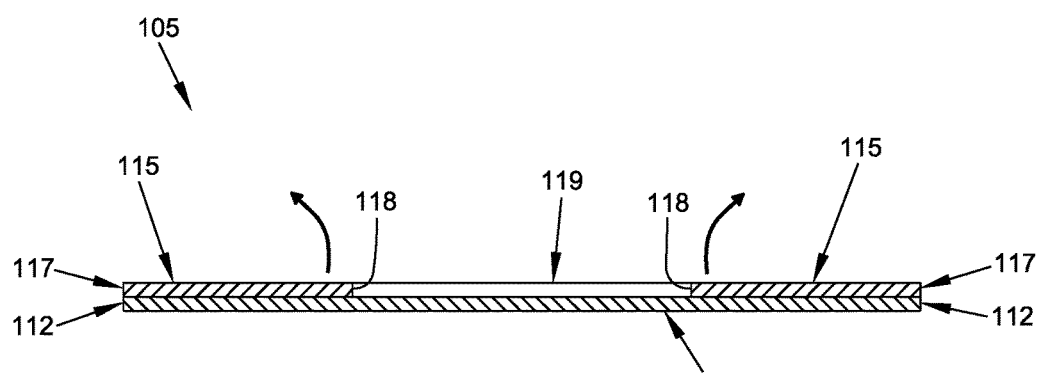
Figure 15:
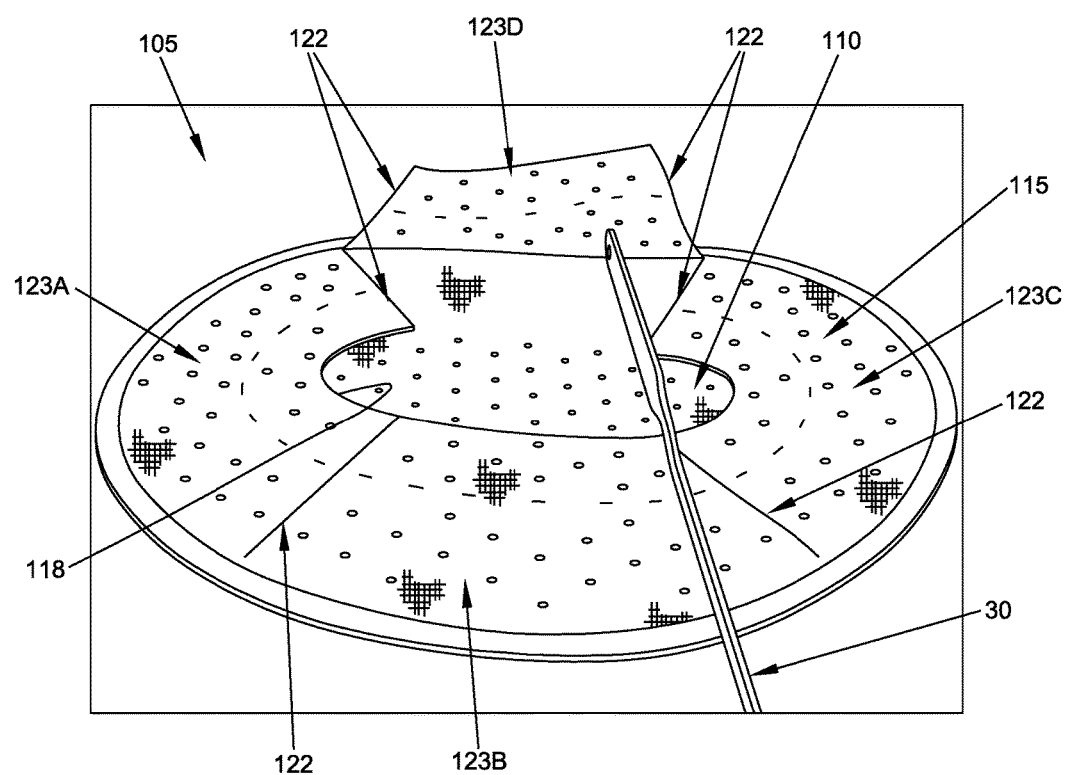
Figure 16:
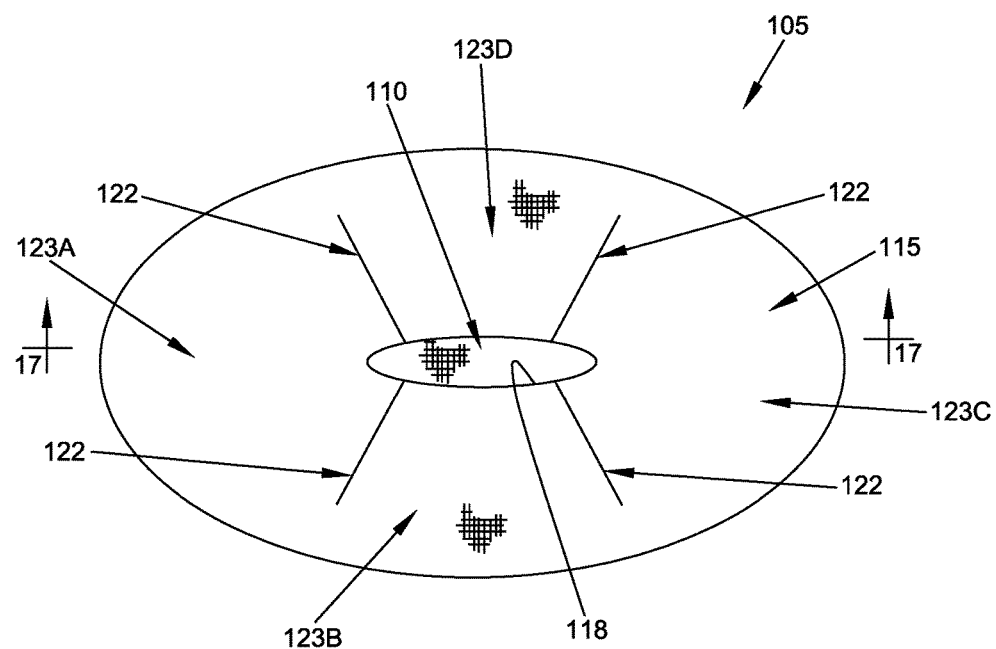
FIGS. 16-18 are schematic views showing another novel segmented skirted surgical mesh formed in accordance with the present invention.
Figure 17:
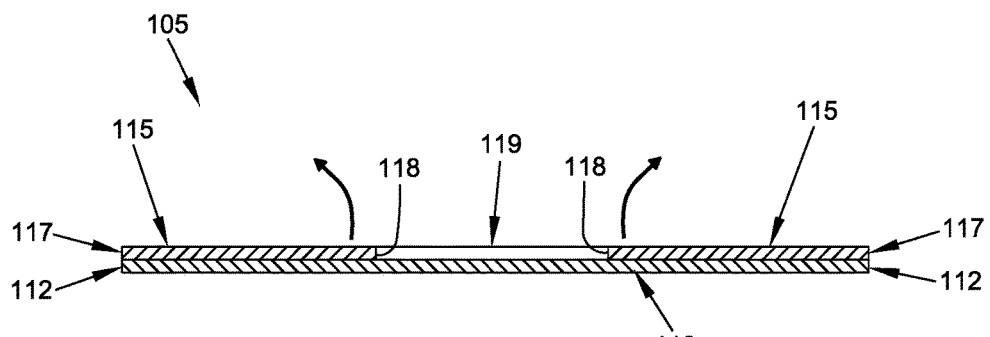
Figure 18:
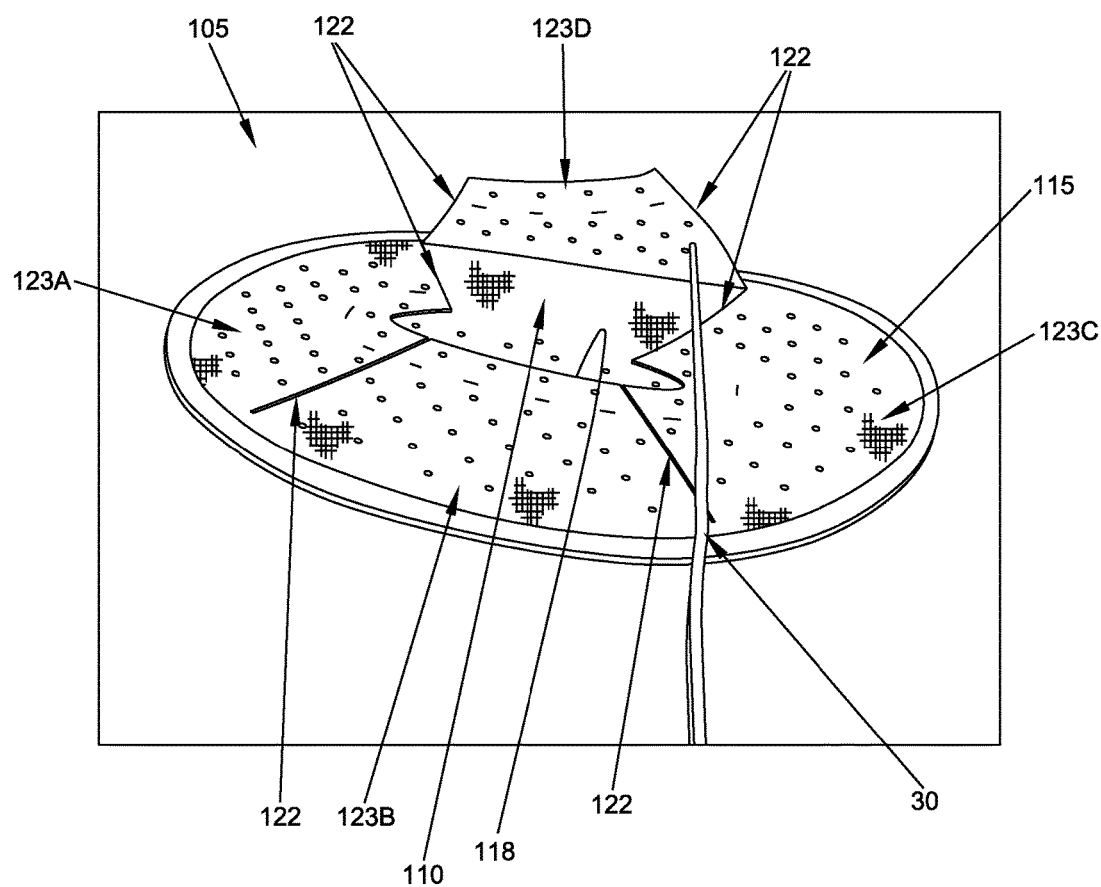

FIGS. 13-15 show another segmented skirted surgical mesh formed in accordance with the present invention. And FIGS. 16-18 show still another segmented skirted surgical mesh formed in accordance with the present invention. Note that with the segmented skirted surgical meshes of FIGS. 13-15 and FIGS. 16-18, segmented continuous skirt or rim 115 is modified so as to provide different sized central openings 119.

The breaks or cuts or slits 122 in segmented continuous skirt or rim 115 preferably extend almost all the way to outer edge 117 of segmented continuous skirt or rim 115, although the breaks or cuts or slits may also extend all the way to outer edge 117 if desired, or may terminate intermediate of segmented continuous skirt or rim 115 if desired.

The number of cuts or breaks or slits 122 formed in segmented continuous skirt or rim 115 of segmented skirted surgical mesh 105, and the placement of those breaks or cuts or slits 122, may be optimized so as to (i) minimize distortion of base layer 110 when a segment or flap 123A, 123B, 123C, etc. is pulled upward, and (ii) minimize the overall number of segments or flaps 123A, 123B, 123C, etc. that the segmented continuous skirt or rim 115 is divided into (since "too many segments or flaps" has the potential to complicate the fixation process for the surgeon). In practice, it is generally preferred to make three or four cuts or breaks or slits 122 in the segmented continuous skirt or rim 115 of segmented skirted surgical mesh 105, whereby to provide three or four segments or flaps 123A, 123B, 123C, etc. in segmented continuous skirt or rim 115 of segmented skirted surgical mesh 105, since providing less than three cuts or breaks or slits 122 in segmented continuous skirt or rim 115 makes it difficult to lift the segments or flaps of continuous segmented skirt or rim 115 away from base layer 110 without distorting base layer 110.

It should also be appreciated that, if desired, outer edge 117 of segmented continuous skirt or rim 115 could terminate inboard of outer edge 112 of base layer 110. Alternatively, outer edge 117 of segmented continuous skirt or rim 115 could overlap outer edge 112 of base layer 110 (e.g., outer edge 117 of segmented continuous skirt or rim 115 could be folded over edge 112 of base layer 110).

By minimizing the distortion of base layer 110 of segmented skirted surgical mesh 105 when one or more of the segments or flaps 123A, 123B, 123C, etc. of segmented continuous skirt or rim 115 is lifted up during fixation, the fixation itself is facilitated, i.e., the fixation will take less time and the final repair geometry is controlled so that there are no gathered areas that might lead to potential sites of discomfort for the patient. Thus, the segmented skirted surgical mesh of the present invention benefits both the surgeon (through facilitated fixation) and the patient (by producing a more cosmetic and comfortable reconstruction).

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A segmented skirted surgical mesh for use in reconstructing a soft tissue defect, said segmented skirted surgical mesh comprising:
a base layer of surgical mesh, said base layer of surgical mesh terminating in an outer edge; and
a segmented skirt of surgical mesh terminating in an outer edge and comprising an inner edge which defines a central opening, said outer edge of said segmented skirt of surgical mesh being secured to said outer edge of said base layer of surgical mesh, and said segmented skirt of surgical mesh comprising a plurality of slits formed in said segmented skirt of surgical mesh, wherein said plurality of slits extend outwardly from said central opening of said segmented skirt of surgical mesh to said outer edge of said segmented skirt of surgical mesh, whereby to form a plurality of flaps of surgical mesh in said segmented skirt of surgical mesh, such that at least one of said flaps of surgical mesh can be lifted away from said base layer of surgical mesh and secured to soft tissue without causing distortion of said base layer of surgical mesh.

2. A segmented skirted surgical mesh according to claim 1 wherein said outer edge of said base layer and said outer edge of said segmented skirt have an oval configuration.

3. A segmented skirted surgical mesh according to claim 1 wherein said outer edge of said base layer and said outer edge of said segmented skirt have a circular configuration.

4. A segmented skirted surgical mesh according to claim 1 wherein three slits are formed in said segmented skirt of surgical mesh.

5. A segmented skirted surgical mesh according to claim 1 wherein four slits are formed in said segmented skirt of surgical mesh.

6. A segmented skirted surgical mesh according to claim 1 wherein each of said slits extends outwardly at an angle of 90 degrees to the central opening of said segmented skirt of surgical mesh.

7. A segmented skirted surgical mesh according to claim 1 wherein each of said slits extends outwardly at an angle of other than 90 degrees to the central opening of said segmented skirt of surgical mesh.

* * * * *